(12) United States Patent
Chen et al.

(10) Patent No.: US 9,976,146 B2
(45) Date of Patent: May 22, 2018

(54) APTAMER TARGETING MAGE-A3 PEPTIDE AND USES THEREOF

(71) Applicant: Academia Sinica, Taipei (TW)

(72) Inventors: Chung-Hsuan Chen, Taipei (TW); Bai-Ling Lin, Taipei (TW); Chin-Yu Wang, Taipei (TW)

( * ) Notice: Subject to any disclaimer, the term of this patent is extended or adjusted under 35 U.S.C. 154(b) by 38 days.

(21) Appl. No.: 15/312,667

(22) PCT Filed: May 29, 2015

(86) PCT No.: PCT/US2015/033115
§ 371 (c)(1),
(2) Date: Nov. 21, 2016

(87) PCT Pub. No.: WO2015/184224
PCT Pub. Date: Dec. 3, 2015

(65) Prior Publication Data
US 2017/0183660 A1 Jun. 29, 2017

Related U.S. Application Data

(60) Provisional application No. 62/005,433, filed on May 30, 2014.

(51) Int. Cl.
*C12N 15/115* (2010.01)
*A61K 47/48* (2006.01)

(52) U.S. Cl.
CPC ...... *C12N 15/115* (2013.01); *A61K 47/48092* (2013.01); *C12N 2310/16* (2013.01); *C12N 2310/315* (2013.01); *C12N 2310/3517* (2013.01); *C12N 2320/32* (2013.01)

(58) Field of Classification Search
None
See application file for complete search history.

*Primary Examiner* — James D Schultz

(57) ABSTRACT

Disclosed herein is an aptamer targeting a MHC-presented peptide and its uses thereof. The MHC-presented peptide is expressed in various cancer cells; therefor, the aptamer of the disclosure is useful as a bio-tool to label and/or treat peptide-presenting cancer cells. Also disclosed herein is a pharmaceutical composition containing the aptamer.

20 Claims, 12 Drawing Sheets

APTAMER TARGETING MAGE-A3 PEPTIDE AND USES THEREOF

BACKGROUND OF THE INVENTION

1. Field of the Invention

The present disclosure relates to an aptamer. More particularly, the present disclosure relates to an aptamer that specifically targets a peptide presented by a major histocompatibility complex (MHC) on the cell surface.

2. Description of Related Art

Aptamers are oligonucleotides, such as ribonucleic acid (RNA) and single-stranded deoxyribonucleic acid (ssDNA), or peptide molecules that can bind to their targets with high affinity and specificity due to their specific secondary and tertiary structures. Generally, the oligonucleotide aptamers are identified from an initial library containing $10^{13}$-$10^{16}$ random RNA or ssDNA sequences through an in vitro selection process termed systematic evolution of ligands by exponential enrichment or the so-called "SELEX procedures."

Like antibodies, oligonucleotide aptamers can be used for both basic research and clinical purposes due to their target-binding specificity. Compared to antibodies, oligonucleotide aptamers offer various advantages, which include, (1) economical synthesis and flexible modification: oligonucleotide aptamers, once selected, can be synthesized in quantity and modified to fulfill various designed purposes via chemical reaction; (2) high stability: oligonucleotide aptamers exhibit long-term stability as dry powders and once dissolved in solution, they are also thermally stable and structurally reversible to their native conformation even after denaturation; (3) high biocompatibility: based on the nucleic acid recognized as self-antigen by immune system, oligonucleotide aptamers are usually low-toxic and low-immunogenic molecules; and (4) rapid tissue penetration: as nucleic acids, oligonucleotide aptamers could easily penetrate and thus bind to the intracellular targets by transfection reagents. These physical and chemical properties make oligonucleotide aptamers a potential targeting-tool to replace antibodies in research, diagnostic platforms, drug discovery, and therapeutics.

Since tumor-associated antigens (TAAs) are only expressed in tumor/cancer cells, they can be considered as tumor markers useful in identifying, labeling, or treating tumor/cancer cells. Melanoma-associated antigen A3 (MAGE-A3) is one of the most frequently and highly expressed TAAs in tumors. It is expressed in 74% of metastatic melanomas, 57% of esophageal carcinoma, 38% of gastric carcinoma, 39% of lung cancer, 33% of multiple myeloma. The expression of MAGE-A3 is also seen in various other types of cancer, including bladder, breast, pancreatic, renal, hepatocellular, and head and neck squamous cell carcinoma. Further, the expression of MAGE-A3 often relates to malignancy and poor prognosis. Therefore, in the fields of cancer therapy or tumor diagnosis, MAGE-A3 serves as a useful marker to precisely and simultaneously target various types of tumors at various stages.

Several epitopes of MAGE-A3 have been identified, and both MHC classes I and II present these antigens. Multiple MAGE-A3 peptide fragments in the region of amino acids 111-126, identified in various tumors, have been associated with a broad set of HLA (human MHC locus) molecules, including alleles of HLA-A, HLA-B, HLA-DP, and HLA-DR, as predominantly observed in various ethnic groups. Thus, these antigens are good candidates for targeting a large population of cancer patients.

In view of the foregoing, there exists a need in the related art an aptamer capable of recognizing a tumor-associated MAGE-A3 peptide with desirable specificity and affinity.

SUMMARY

The following presents a simplified summary of the disclosure in order to provide a basic understanding to the reader. This summary is not an extensive overview of the disclosure and it does not identify key/critical elements of the present invention or delineate the scope of the present invention. Its sole purpose is to present some concepts disclosed herein in a simplified form as a prelude to the more detailed description that is presented later.

As embodied and broadly described herein, the present disclosure features an oligonucleotide aptamer capable of targeting a peptide, a composition containing the peptide-targeting oligonucleotide aptamer, and their uses in targeting a cell having the peptide presented by MHC on its surface. Furthermore, based on the targeting capability, the oligonucleotide aptamer can be conjugated with an anti-cancer drug and thus be used to treat a tumor with the peptide presented by MHC on its surface.

One aspect of the present disclosure is directed to an oligonucleotide aptamer for targeting a peptide presented by a MHC molecule. According to one embodiment, the peptide has the amino acid sequence of SEQ ID NO: 4. In one specific embodiment, the oligonucleotide aptamer comprises the sequence of AGCACTCAATATTCCC (SEQ ID NO: 1). In another specific embodiment, the oligonucleotide aptamer further comprises an upstream sequence of ATCCAGAGTGACGCAGCA (SEQ ID NO: 2) and a downstream sequence of TGGACACGGTGGCTTAGT (SEQ ID NO: 3).

In some embodiments of the present disclosure, the peptide is a tumor-associated peptide and is derived from MAGE-A3.

In another aspect, the present disclosure provides a composition comprising the peptide-targeting oligonucleotide aptamer as described above, and a pharmaceutically acceptable excipient.

According to some embodiments of the present disclosure, the peptide is expressed in a tumor selected from the group consisting of melanomas, leukemia, tongue carcinoma, colorectal carcinoma, esophageal carcinoma, gastric carcinoma, lung cancer, multiple myeloma, bladder cancer, breast cancer, pancreatic cancer, renal cancer, hepatocellular carcinoma, ovarian cancer, prostate cancer, and head and neck squamous cell carcinoma.

According to embodiments of the present disclosure, the oligonucleotide aptamer is modified with one or more chemical groups to enhance the stability of the oligonucleotide aptamer, wherein the chemical group is any of 2'-aminopyrimidinyl group, 2'-O-methylpurinyl group, 5'-dialkyl group, phosphorothioate cap, 2'-OH nucleotides, 2'-fluoropyrimidine or 5-(1-pentynyl)-2'-deoxyuridine. In one specific example, the oligonucleotide aptamer is modified with phosphorothioate cap.

According to some embodiments of the present disclosure, the oligonucleotide aptamer is conjugated with a fluorescent dye, a reporter molecule, a contrast agent, an anti-cancer drug, a peptide or a particle. In some embodiments of the present disclosure, the oligonucleotide aptamer is conjugated with an iron oxide magnetic particle. In other embodiments of the present disclosure, the oligonucleotide aptamer is conjugated with a fluorescent dye.

In still another aspect, the present disclosure pertains to the uses of the oligonucleotide aptamer and the composition comprising the same. For example, the oligonucleotide aptamer and the oligonucleotide aptamer-containing composition can be used in methods for targeting the peptide-presenting cells. In one specific example, the peptide is derived from MAGE-A3 and is presented on the cell surface by a MHC molecule.

According to the embodiments of the present disclosure, a method of targeting a peptide-presenting cell using the oligonucleotide aptamer-containing composition of the present disclosure is provided. The method includes the step of: incubating the peptide-presenting cell with a sufficient amount of the composition of the invention, so as to allow the oligonucleotide aptamer of the invention to bind to the peptide-presenting cell, in which the peptide-presenting cell is a tumor cell selected from the group consisting of melanomas, leukemia, tongue carcinoma, colorectal carcinoma, esophageal carcinoma, gastric carcinoma, lung cancer, multiple myeloma, bladder cancer, breast cancer, pancreatic cancer, renal cancer, hepatocellular carcinoma, ovarian cancer, prostate cancer, and head and neck squamous cell carcinoma. According to some embodiments of the present disclosure, the peptide is presented by the MHC molecule and is derived from MAGE-A3.

In some embodiments of the present disclosure, the oligonucleotide aptamer comprised in the composition for targeting the peptide-presenting cell is modified with one or more chemical groups so as to enhance the stability of the oligonucleotide aptamer, in which the chemical group is any of 2'-aminopyrimidinyl group, 2'-O-methylpurinyl group, 5'-dialkyl group, phosphorothioate cap, 2'-OH nucleotides, 2'-fluoropyrimidine or 5-(1-pentynyl)-2'-deoxyuridine. In one specific example, the oligonucleotide aptamer is modified with phosphorothioate cap.

According to some embodiments of the present disclosure, for various purposes, the oligonucleotide aptamer comprised in the composition for targeting the peptide-presenting cell is able to be conjugated with a fluorescent dye, a reporter molecule, a contrast agent, an anti-cancer drug, a peptide or a particle. In some embodiments of the present disclosure, the oligonucleotide aptamer is conjugated with an iron oxide magnetic particle. In one example, the oligonucleotide aptamer is conjugated with a fluorescent dye.

According to a further aspect, the present disclosure provides a method of treating a subject suspected of having or suffering from a tumor having a tumor-associated peptide presented therein. The method includes step of: administering to the subject a therapeutically effective amount of the composition of the invention to alleviate or ameliorate the progression of the tumor, wherein the oligonucleotide aptamer of the invention is conjugated with an anti-cancer drug; in which the tumor is selected from the group consisting of melanomas, leukemia, tongue carcinoma, colorectal carcinoma, esophageal carcinoma, gastric carcinoma, lung cancer, multiple myeloma, bladder cancer, breast cancer, pancreatic cancer, renal cancer, hepatocellular carcinoma, ovarian cancer, prostate cancer, and head and neck squamous cell carcinoma. According to the embodiments of the present disclosure, the tumor-associated antigen is a MAGE-A3 peptide presented by the MHC molecule.

According to one embodiment, the anti-cancer drug conjugated with the oligonucleotide aptamer of the present disclosure can be mechlorethamine, cyclophosphamide, melphalan, chlorambucil, ifosfamide, busulfan, N-Nitroso-N-methylurea, carmustine, lomustine, semustine, fotemustine, streptozotocin, dacarbazine, mitozolomide, temozolomide, thiotepa, mytomycin, diaziquone, cisplatin, carboplatin, oxaliplatin, methotrexate, pemetrexed, fluorouracil, capecitabine, cytarabine, gemcitabine, decitabine, vidaza, fludarabine, nelarabine, cladribine, clofarabine, pentostatin, thioguanine, mercaptopurine, vinca alkaloids, taxanes, irinotecan, topotecan, etoposide, doxorubicin, mitoxantrone, teniposide, novobiocin, merbarone, aclarubicin, anthracyclines, actinomycin, bleomycin, plicamycin, or mitomycin.

The oligonucleotide aptamer comprised in the present composition for treating the peptide-presenting tumor can be modified with one or more chemical groups that is any of 2'-aminopyrimidinyl group, 2'-O-methylpurinyl group, 5'-dialkyl group, phosphorothioate cap, 2'-OH nucleotides, 2'-fluoropyrimidine or 5-(1-pentynyl)-2'-deoxyuridine, to enhance the stability of the oligonucleotide aptamer. In one specific example, the oligonucleotide aptamer is modified with phosphorothioate cap.

Many of the attendant features and advantages of the present disclosure will become better understood with reference to the following detail description.

BRIEF DESCRIPTION OF THE DRAWINGS

The present description will be better understood from the following detailed description read in light of the accompanying drawings, where.

Figure 1:
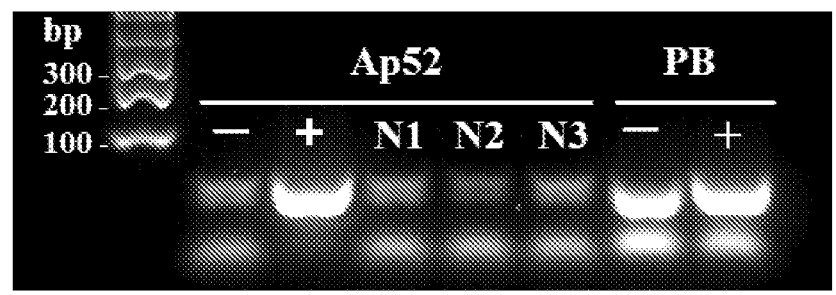
FIG. 1 is a photograph illustrating the PCR results of the binding affinity and specificity between Ap52 of Example 2 and specified peptides, in which peptide MAGE-A3$_{111-125}$ (+), NY-ESO-1$_{119-143}$ (N1), NY-ESO-1$_{157-170}$ (N2), NY-ESO-1$_{87-111}$ (N3), or no peptide (−) were reacted with Ap52, followed by elution and PCR amplification; PB served as a control of oligonucleotide aptamer.

In accordance with common practice, the various described features/elements are not drawn to scale but instead are drawn to best illustrate specific features/elements relevant to the present invention.

DETAILED DESCRIPTION OF PREFERRED EMBODIMENTS

The detailed description provided below in connection with the appended drawings is intended as a description of the present examples and is not intended to represent the only forms in which the present example may be constructed or utilized. The description sets forth the functions of the examples and the sequence of steps for constructing and operating the examples. However, the same or equivalent functions and sequences may be accomplished by different examples.

The terms "a", "an", and "the" as used herein are defined to mean "one or more" and include plural referents unless the context clearly dictates otherwise.

The term "oligonucleotide" as used herein refers to a polydeoxyribonucleotides (containing 2'-deoxy-D-ribose or modified forms thereof), i.e., DNA, to polyribonucleotides (containing D-ribose or modified forms thereof), i.e., RNA, and to any other type of polynucleotide which is an N-glycoside or C-glycoside of a purine or pyrimidine base, or modified purine or pyrimidine base or a basic nucleotides.

As used herein, the term "aptamer" or "oligonucleotide aptamers" refer to oligonucleotides having specific binding regions which are capable of forming complexes with an intended target molecule in an environment wherein other substances in the same environment are not complexed to the oligonucleotide, and the oligonucleotides denote both singular and plural sequences of oligonucleotides, as defined hereinabove.

The specificity of the binding is defined in terms of the comparative dissociation constants ($K_d$) of the aptamer for target as compared to the dissociation constant with respect to the aptamer and other materials in the environment or unrelated molecules in general. Typically, the $K_d$ between the aptamer and the target will be 2-fold, preferably 5-fold, more preferably 10-fold less than the $K_d$ between the target and other unrelated material or accompanying material in the environment. Even more preferably the $K_d$ will be 50-fold less, more preferably 100-fold less, and more preferably 200-fold less than the $K_d$ between the target and the unrelated material or accompanying material in the environment. The value of this dissociation constant can be determined directly by well-known methods.

As used herein, a "pharmaceutically acceptable excipient" is one that is suitable for use with the subjects without undue adverse side effects (such as toxicity, irritation, and allergic response) commensurate with a reasonable benefit/risk ratio. Also, each excipient must be "acceptable" in the sense of being compatible with the other ingredients of the pharmaceutical composition. The excipient can be in the form of a solid, semi-solid, or liquid diluent, cream or a capsule.

As used herein, the term "treating" encompasses partially or completely preventing, ameliorating, mitigating and/or managing a symptom, a secondary disorder or a condition associated with MAGE-A3-expressing tumors. The term "treating" as used herein refers to application or administration of the MAGE-A3 peptide-targeting oligonucleotide aptamer that is conjugated with an anti-cancer drug, or the composition comprising the same in accordance with the present disclosure, to a subject, who has a symptom, a secondary disorder, or a condition associated with MAGE-A3-expressing tumors, with the purpose to partially or completely alleviate, ameliorate, relieve, delay onset of, inhibit progression of, reduce severity of, and/or reduce incidence of one or more symptoms, secondary disorders or features of MAGE-A3-expressing tumors. Symptoms, secondary disorders, and/or conditions associated with MAGE-A3-expressing tumors include, but are not limited to, unexplained weight loss, fever, fatigue, pain, and change in physical function. Treatment may be administered to a subject who exhibits only early signs of such symptoms, disorder, and/or condition for the purpose of decreasing the risk of developing the symptoms, secondary disorders, and/or conditions associated with MAGE-A3-expressing tumors. Treatment is generally "effective" if one or more symptoms or clinical markers are reduced as that term is defined herein. Alternatively, a treatment is "effective" if the progression of a symptom, disorder or condition is reduced or halted.

The term "therapeutically effective amount" as used herein refers to the quantity of a component (such as the anti-cancer drug conjugated oligonucleotide aptamer of the present invention) which is sufficient to yield a desired response. The specific effective amount will vary with such factors as the particular condition being treated, the physical condition of the subject (e.g., the subject's body mass, age, or gender), the type of mammal or animal being treated, the duration of the treatment, the nature of concurrent therapy (if any), and the specific formulations employed. A therapeutically effective amount is also one in which any toxic or detrimental effects of the component or composition are outweighed by the therapeutically beneficial effects. Effective amount may be expressed, for example, in grams, milligrams or micrograms or as milligrams per kilogram of body weight (mg/kg). Alternatively, the effective amount can be expressed in the concentration of the active component in the pharmaceutical composition, such as molar concentration, mass concentration, volume concentration, molality, mole fraction, mass fraction and mixing ratio. Specifically, the term "therapeutically effective amount" used in connection with the anti-cancer drug conjugated oligonucleotide aptamer described herein refers to the quantity of the anti-cancer drug conjugated oligonucleotide aptamer, which is sufficient to alleviate or ameliorate the progression of the tumor in the subject.

The term "subject" refers to a mammal including the human species that is treatable with the oligonucleotide aptamer, the composition comprising the same and/or methods of the present invention. The term "subject" is intended to refer to both the male and female gender unless one gender is specifically indicated.

In the present disclosure, the peptide-presenting cell refers to the cell that expresses the peptide; preferably, the peptide-presenting cell refers to the cell that has the peptide presented by MHC on its surface. Similarly, the peptide-presenting tumor refers to the tumor that expresses the peptide; preferably, the peptide-presenting tumor refers to the tumor that comprises the cell having the peptide presented by MHC on its surface.

The practices of this invention are hereinafter described in detail with respect to an oligonucleotide aptamer against a peptide presented by a MHC molecule, a composition containing the peptide-targeting oligonucleotide aptamer, and their uses in targeting the peptide-presenting cells and/or in treating the peptide-presenting tumors while the peptide-targeting oligonucleotide aptamer is further conjugated with an anti-cancer drug. According to some embodiments of the present disclosure, the peptide is derived from MAGE-A3.

Systematic evolution of ligands by exponential enrichment (SELEX) was performed to obtain an oligonucleotide aptamer that specifically targets a peptide (e.g., MAGE-A3$_{111-125}$ peptide). In general, a very large oligonucleotide library (approximately $10^{13}$-$10^{16}$ random RNA or ssDNA sequences) was first synthesized, in which the library was consisting of randomly generated sequences of fixed length flanked by constant 5'- and 3'-ends that serve as primers. After exposing the synthesized library to the target peptide (e.g., MAGE-A3$_{111-125}$ peptide), the oligonucleotides specifically bound to the target were evaluated and amplified by polymerase chain reaction (PCR). Several rounds of such binding-selection were repeated to increase the stringency of the elution conditions, thus obtaining the highest binding affinity sequences.

The selected oligonucleotide aptamers are highly specific to the target peptide. According to one aspect of the present disclosure, an oligonucleotide aptamer targeting the MAGE-A3 peptide is provided, wherein the oligonucleotide aptamer consists of 16 nucleotides of AGCACTCAATATTCCC (hereinafter "Ap16", SEQ ID NO: 1), and the MAGE-A3 peptide has the amino acid sequence of SEQ ID NO: 4.

According to another embodiment of the present disclosure, the oligonucleotide aptamer Ap16 further comprises an upstream sequence of ATCCAGAGTGACGCAGCA (SEQ ID NO: 2) and a downstream sequence of TGGACACGGTGGCTTAGT (SEQ ID NO: 3). The resulting oligonucleotide aptamer has a length of 52 nucleotides and is thus designated as "Ap52".

In embodiments of the present disclosure, both Ap16 and Ap52 bind to the MAGE-A3 peptide with $K_d$ values in the nanomolar range.

In another aspect, the obtained oligonucleotide aptamer (i.e., Ap16 or Ap52) with capability of specifically binding to the MAGE-A3 peptide may thus be formulated into a composition that targets MAGE-A3 peptide-presenting cells. The MAGE-A3 peptide is a tumor-associated antigen (TAA) and presented in different types of tumors selected from the group consisting of melanomas, leukemia, tongue carcinoma, colorectal carcinoma, esophageal carcinoma, gastric carcinoma, lung cancer, multiple myeloma, bladder cancer, breast cancer, pancreatic cancer, renal cancer, hepatocellular carcinoma, ovarian cancer, prostate cancer, and head and neck squamous cell carcinoma. Thus, the MAGE-A3 peptide-targeting oligonucleotide aptamer and the composition comprising the same is a useful bio-tool to label and/or treat cancer cells with the MAGE-A3 expression.

According to some embodiments of the present disclosure, the MAGE-A3 peptide is presented by a MHC molecule. In one embodiment, the MAGE-A3 peptide is presented by a MHC class I molecule. In another embodiment, the MAGE-A3 peptide is presented by a MHC class II molecule.

In addition to the present oligonucleotide aptamer (i.e., Ap16 or Ap52), the composition further comprises a pharmaceutically acceptable excipient. The choice of a pharmaceutically acceptable excipient to be used in conjunction with the present oligonucleotide aptamer is basically determined by the desired product form of the pharmaceutical or health care composition.

According to embodiments of the present disclosure, Ap16 or Ap52 is modified with one or more chemical groups, so as to enhance the stability of the oligonucleotide aptamer. Most oligonucleotide aptamer can be modified with suitable chemical groups during chemical synthesis of nucleic acid, depending on the specific purposes of application. Suitable chemical groups for modifying the oligonucleotide aptamer (e.g., Ap16 and Ap56) include, but are not limited to, 2'-aminopyrimidinyl group, 2'-O-methylpurinyl group, 5'-dialkyl group, phosphorothioate cap, 2'-OH nucleotides, 2'-fluoropyrimidine and 5-(1-pentynyl)-2'-deoxyuridine. In one specific embodiment, Ap16 or Ap52 is modified with phosphorothioate cap.

In other embodiments of the present disclosure, for the detection or treatment purpose, Ap16 or Ap52 is further conjugated with a fluorescent dye, a reporter molecule, a contrast agent, an anti-cancer drug, a peptide or a particle. The conjugation can be achieved by the methods familiar with a skilled artisan. For example, the 3' or 5' primary amines can be coupled to various molecules during chemical synthesis of nucleic acid; or the conjugation can via classic carbodiimide, aldehyde, diazonium, or other approaches which take advantage of the much greater chemical reactivity of primary alkyl amine tags versus aryl amines on the nucleotides themselves.

According to one embodiment, Ap16 or Ap52 is conjugated with an iron oxide magnetic particle. According to another embodiment, Ap16 or Ap52 is conjugated with a fluorescent dye. According to still another embodiment, Ap16 or Ap52 is conjugated with an anti-cancer drug.

Cyanines are fluorescent dyes, which are preferred over the conventional dyes, such as Fluorescein (FITC) and rhodamines (TRITC, RRX), due to their brightness and more stable fluorescence signals. Among the Cyanines, Cyanine 3 (Cy3) and Cyanine 5 (Cy5) are the most popular. Cy3 emits orange fluorescence (~550 nm excitation, ~570 nm emission), while Cy5 emits fluorescence that is in the red region (~650/670 nm), but absorbs in the orange region (~649 nm). Cy3 can be detected by various fluorometers, imagers, and microscopes with standard filters for Tetramethylrhodamine (TRITC). Due to inherently high extinction coefficient, this dye is also easily detected by naked eye on gels, and in solution. Accordingly, in some analytic assays of the present disclosure that are employed to characterize the binding/targeting between the oligonucleotide aptamer and MAGE-A3 peptide-presenting cell, Cy3 is chosen as the fluorescent dye conjugated with Ap16 or Ap52.

Suitable anti-cancer drug conjugated with Ap16 or Ap52 includes, but is not limited to, alkylating agents (such as, mechlorethamine, cyclophosphamide, melphalan, chlorambucil, ifosfamide, busulfan, N-Nitroso-N-methylurea, carmustine, lomustine, semustine, fotemustine, streptozotocin, dacarbazine, mitozolomide, temozolomide, thiotepa, myotomycin, diaziquone, cisplatin, carboplatin, and oxaliplatin), anti-metabolites (such as, methotrexate, pemetrexed, fluorouracil, capecitabine, cytarabine, gemcitabine, decitabine, vidaza, fludarabine, nelarabine, cladribine, clofarabine, pentostatin, thioguanine, and mercaptopurine), anti-microtubule agents (such as, vinca alkaloids and taxanes), topoisomerase inhibitors (such as, irinotecan, topotecan, etoposide, doxorubicin, mitoxantrone, teniposide, novobiocin, merbarone, and aclarubicin), and cytotoxic antibiotics (such as, anthracyclines, actinomycin, bleomycin, plicamycin, and mitomycin).

According to one embodiment of the present disclosure, both the phosphorothioate modification and fluorescent dye conjugation can efficiently improve the oligonucleotide aptamer (i.e., Ap16 and Ap52) stability.

Another aspect of the present disclosure is directed to uses of Ap16, or Ap52, which includes the methods of targeting the MAGE-A3 peptide-presenting cells and/or treating the MAGE-A3 peptide-presenting tumors.

According to embodiments of the present disclosure, a method of targeting the MAGE-A3 peptide-presenting cells using Ap16- or Ap52-containing composition of the present disclosure is provided. The method includes the step of: incubating a sufficient amount of the composition of the invention with the MAGE-A3 peptide-presenting cell, so as to allow the oligonucleotide aptamer of the invention to bind to the MAGE-A3 peptide-presenting cell; wherein the MAGE-A3 peptide-presenting cell is a tumor cell, in which the tumor is selected from the group consisting of melanomas, leukemia, tongue carcinoma, colorectal carcinoma, esophageal carcinoma, gastric carcinoma, lung cancer, multiple myeloma, bladder cancer, breast cancer, pancreatic cancer, renal cancer, hepatocellular carcinoma, ovarian cancer, prostate cancer, and head and neck squamous cell carcinoma.

In some embodiments of the present disclosure, Ap16 or Ap52 of the present composition is modified with one or more chemical groups to enhance the stability of the oligonucleotide aptamer, wherein the chemical group is any of 2'-aminopyrimidinyl group, 2'-O-methylpurinyl group, 5'-dialkyl group, phosphorothioate cap, 2'-OH nucleotides, 2'-fluoropyrimidine or 5-(1-pentynyl)-2'-deoxyuridine. In one example, Ap16 or Ap52 of the present composition is modified with phosphorothioate cap.

According to some embodiments of the present disclosure, Ap16 or Ap52 of the present composition is conjugated with a fluorescent dye, a reporter molecule, a contrast agent, an anti-cancer drug, a peptide or a particle. In some embodiments of the present disclosure, Ap16 or Ap52 of the composition of the invention is conjugated with an iron oxide magnetic particle. According to some embodiments of the present disclosure, Ap16 or Ap52 of the composition of the invention is conjugated with a Cy3 fluorescent dye.

The targeting of Ap16 or Ap52 to the MAGE-A3 peptide-presenting cell can be detected by different methods in accordance with the conjugated molecules. For example, the fluorescent dye (e.g., Cy3)-conjugated Ap16 or Ap52 can be detected by fluorescent microscopy or flow cytometry assay.

The amount of the present composition sufficient to bind to the MAGE-A3-expressing cell is about 100-1000 nM; that is, the amount can be 100, 200, 300, 400, 500, 600, 700, 800, 900, or 1000 nM. Preferably, the amount is about 300-500 nM. In one specific example, the amount of the composition used to detect the expression of MAGE-A3 is 400 nM.

According to a further aspect, the present disclosure provides a method of treating a subject suspected of having or suffering from a tumor having a MAGE-A3 antigen presented therein. The method includes the step of: administering to the subject a therapeutically effective amount of the composition of the invention, to alleviate or ameliorate the progression of the tumor, in which the oligonucleotide aptamer of the invention is conjugated with an anti-cancer drug.

As discussed above, the oligonucleotide aptamer (e.g., Ap16 or Ap52) conjugated with an anti-cancer drug can be modified with suitable chemical groups so as to enhance its stability. For example, the oligonucleotide aptamer can be modified with phosphorothioate cap.

The following examples illustrate the identification of MAGE-A3 peptide-targeting aptamer of the present invention and the use thereof in the target and/or treatment of cancer cells with MAGE-A3 expression. The examples are illustrative only, and do not limit the scope of the present invention.

EXAMPLES

Materials and Methods
Cell Culture
The tongue carcinoma cell line Cal-27 (ATCC: CRL-2095), colorectal adenocarcinoma cell line DLD-1 (ATCC: CCL-221), hepatocellular carcinoma cell line HepG2 (ATCC: HB-8065), breast adenocarcinoma cell line MCF-7 (ATCC: HTB-22), and oral mucosal fibroblasts (OMF) were cultured in Dulbecco's modified Eagle's medium (DMEM). The chronic myelogenous leukemia K-562 (ATCC: CCL-243), lung carcinoma cell line A549 (ATCC: CCL-185) and pancreas adenocarcinoma cell line AsPC-1 (ATCC: CRL- 1682) were cultured in Roswell Park Memorial Institute medium (RPMI). The malignant melanoma cell line SK-MEL-28 (ATCC: HTB-72) were cultured in Minimum Essential Medium (MEM). Each culture media contained 10% fetal bovine serum (FBS) and 1× Penicillin-Streptomycin-Glutamine. The fibrocystic disease cell line MCF-10A (ATCC: CRL-10317) were cultured in DMEM containing 5% horse serum, 20 ng/ml EGF, 0.5 mg/ml hydrocortisone, 100 ng/ml cholera toxin, 20 μg/ml insulin and 1× Penicillin-Streptomycin-Glutamine. The normal human epidermal melanocyte primary cell line HEM-a (ScienCell, USA) was cultured in Melanocyte Medium (MeIM, ScienCell, USA) in a poly-L-lysine-coated T-75 flask. The normal human bronchial epithelial cell line BEAS-2B (ATCC: CRL-9609) and normal human liver epithelial cell line THLE-3 (ATCC: CRL-11233) were cultured in BEGM in a pre-coated T-75 flask with a mixture of 0.01 mg/ml fibronectin, 0.03 mg/ml bovine collagen type I and 0.01 mg/ml bovine serum albumin dissolved in BEBM. The normal human colon epithelial cell line FHC (ATCC: CRL-1831) was cultured in DMEM/F12 Medium containing extra 10 mM HEPES, 0.005 ng/ml hydrocortisone, 10 ng/ml cholera toxin, 0.005 ng/ml insulin, 0.005 mg/ml transferrin and 10% FBS. The normal human pancreas epithelial-like cell line hTERT-HPNE (ATCC: CRL-4023) was cultured in 75% DMEM without glucose, 25% Medium M3 Base containing 5% FBS, 10 ng/ml EGF, 5.5 mM D-glucose and 750 ng/ml puromycin. All cells were cultured in a 5% $CO_2$-humidified chamber at 37° C., and when 90% confluent, trypsin/EDTA and trypsin neutralization solutions (ScienCell Research Laboratories, USA) were added to harvest the cells.

Cell Transfection

GFP-tagged human HLA cDNA clones, HLA I (HLA-A, Cat. No. RG200661) and HLA II (HLA-DRB4, Cat. No. RG202743), in pCMV6-AC-GFP vector, were obtained from OriGene Technologies, USA. Plasmid DNA was extracted with PureLink® HiPure Plasmid Midiprep Kit (Life Technologies, USA), and transfected into K-562 cells using Lipofectamine® 3000 Transfection Reagent (Life Technologies, USA). The transfected cells were grown in RPMI 1640 containing 10% FBS and 250 μg/ml G418 for 3 days and used in the binding assay with flow cytometry.

Confocal Microscopy

A confocal laser-scanning microscope (TCS-SP5-MP-SMD, Leica) was used to acquire the cell images. The cells were seeded onto Millicell EZ SLIDE 8-well glass slides (Merck Millipore). Fresh culture medium was replaced after 24 hr. The cytoplasm of the cells was stained using Calcein AM (Excitation wavelength: 488 nm, Molecular Probes), diluted 2000 times in culture medium, in the culture oven for 30 minutes, followed by washing twice with washing buffer. DNA (300 nM) conjugated with Cy3 (Excitation wavelength: 520 nm, Molecular Probes) was denatured in 50 μl of binding buffer at 95° C. for 5 minutes and cooled on ice for 30 minutes. Subsequently, 150 μl of cold binding buffer was added, and the mixture was incubated at room temperature. The adherent cells were incubated with Cy3-conjugated DNA solution in a total of 200 μl of binding buffer for two hours at room temperature with shaking at 60 rpm. The cells were subsequently washed three times with 200 μl of washing buffer for 10 min with shaking to remove the unbound conjugates. Subsequently, the cells were fixed by incubating with 3.7% formaldehyde solution for 10 min. After washing three times with a washing buffer, the nucleus was stained with 4', 6-diamidino-2-phenylindole dihydrochloride (DAPI, Excitation wavelength: 405 nm) for 20 minutes. After washing cells three times with washing buffer, fluorescence images of the cells were obtained under a confocal microscope.

Immunoblot Analysis

The cell lysates were separated in 12% SDS-PAGE, and the MAGE-A3 protein was detected on protein gel blots using anti-MAGE-A3 mAb (Clone 2F10, OriGene Technologies, USA) and HRP-conjugated goat anti-mouse IgG (H+L) secondary antibody (ThermoFisher Scientific, USA). The immunoreacting images were detected by ImageQuant LAS 4000 (GE Healthcare Life Sciences, USA).

Isothermal Titration Calorimetry (ITC) for Dissociation Constant ($K_d$) Determination Thermodynamic profile of the interaction between DNA and peptide was measured with a MicroCal iTC$_{200}$ (GE Healthcare Life Sciences) at 25° C. in washing buffer (0.45% glucose, 5 mM $MgCl_2$, in Dulbecco's Phosphate-Buffered Saline). The unmodified MAGE-A3$_{111-125}$ peptide (0.3 mM, 200 μl) was titrated with 18 successive injections of 2 μl aptamer (0.1 mM) at 150 s intervals. The data were analyzed using MicroCal Origin 7 and fit with a one-set-of sites binding model to obtain values of enthalpy change (ΔH) and association constant ($K_a$).

Flow Cytometry

Cells were washed twice with washing buffer (0.45% glucose, 5 mM $MgCl_2$, in Dulbecco's Phosphate-Buffered Saline) at 37° C. The Cy3-conjugated Ap52 aptamer at a concentration of 400 nM was incubated with 1×10$^6$ cells at room temperature for two hours. After washing with 200 μl of washing buffer three times, cells were resuspended in 400 μl of washing buffer. The fluorescence intensity was determined with a BD FACSAria Ilu flow cytometer (BD Biosciences, USA) by counting 50,000 events. The flow cytometry analysis was performed in triplicate for each cell line. The untreated cells were used as controls.

Nuclease Resistance Assay

Nuclease resistance assay of aptamers was conducted in 10% FBS diluted with DMEM at 37° C. Half microgram of each aptamer (i.e., Ap52; ThioAp52: A*TCCAGA G*TGACGCAGCA-A*GCACTCA*ATATTCC*C-TGGACACG*GTGGCTTAG*T, in which *=phosphorothioate modification site; Cy3-conjugated Ap52; and Cy3-conjugated ThioAp52) was evaporated to dryness under reduced pressure and then incubated with 300 ml 10% FBS/DMEM at 37° C. At 0, 1, 2, 6, 12 and 24 hr, 50 ml of samples were collected and stored at −20° C. for at least 20 min. The samples were evaporated to dryness and then 10 μl of gel loading buffer and 10 μl of autoclaved water was added. 10 μl of the mixture was used for PAGE, which was carried out at room temperature using 18% polyacrylamide gel in 0.5× TBE buffer (Tris-borate-EDTA). The degradation intensity on the gel was analyzed using ImageJ software.

Example 1

Identifying MAGE-A3 Targeting Aptamer by SELEX Procedure

The oligonucleotide aptamer specifically targeting MAGE-A3 was selected by SELEX procedure. All the random oligonucleotide library and oligonucleotides used in the present disclosure, including biotin or Cy3 conjugates, and biotinylated conjugates, were custom-made at Genomics BioSci & Tech (Taipei, Taiwan). Streptavidin-coupled magnetic beads (Dynabeads® My One™ Streptavidin C1) were purchased from Life Technologies.

The random oligonucleotide library was used for in vitro selection by magnetic bead-based methods. The library comprised $10^{15}$ 52-mer molecules. Each of the 52-mer molecules comprises in sequence: a 5'-end primer of 18 nucleotides (ATCCAGAGTGACGCAGCA, SEQ ID NO: 2), a central random region of 16 nucleotides, and a 3'-end primer of 18 nucleotides (TGGACACGGTGGCTTAGT, SEQ ID NO: 3). Streptavidin-coupled magnetic beads, $10^7$ in 10 µl, were washed twice with washing buffer (0.45% glucose, 5 mM $MgCl_2$, in Dulbecco's Phosphate-Buffered Saline) to remove residual preservatives and solvents. The beads were subsequently incubated with biotinylated peptide MAGE-A3$_{111-125}$ (RKVAELVHFLLLKYR, SEQ ID NO: 4) in washing buffer at room temperature for one hour with stirring and shaking at a speed of 99 rpm. The ratio of MAGE-A3$_{111-125}$ peptides to streptavidin-coated magnetic beads was adjusted to 10:1 in a total volume of 100 µl. The unbound peptides were removed by washing the beads twice with washing buffer. The unbound positions of streptavidin were blocked with 100 µl of biotin solution (1 mg/ml) for 30 minutes under the afore-mentioned incubation conditions. The peptide-magnetic bead complexes were washed three times with binding buffer (0.01% yeast tRNA, 0.1% BSA, in washing buffer) to remove free biotin and excess ionic species, and used in the following selection.

Streptavidin-coupled magnetic beads were employed to remove any non-specifically bound oligonucleotides. The remaining oligonucleotides were recovered using a molecular weight cut-off column (3,000 MWCO PES, Sartorius), vacuum-dried at room temperature, dissolved in 50 µl binding buffer, and used as the input ssDNA library.

The library was denatured at 95° C. for five minutes and cooled on ice for 30 minutes. The binding reaction between the library and MAGE-A3$_{111-125}$-magnetic bead complexes was allowed to proceed for 1 hour at room temperature with constant stirring and shaking. DNA-peptide-magnetic bead complexes were collected using a magnet. After washing 3 times with 100 µl of washing buffer, the bound DNA was eluted with 95° C. pure water, and PCR amplified using a 5'-end primer having the sequence of SEQ ID NO: 2 and a 3'-end primer having the sequence of SEQ ID NO: 3 for 10 cycles of 95° C. for 150 s; 95° C. for 30 s; 56.3° C. for 30 s; 72° C. for 30 s; and 72° C. for 180 s using PfuUltra High-Fidelity DNA Polymerase (Merck, Taiwan). The PCR product (dsDNA) was used as template in subsequent anchored PCR using a forward primer labeled at the 5'-end with biotin under the same thermocycling conditions as described above.

After amplification, the reaction mixtures were pooled (500 µl total) together, and the 5'-biotin was removed from the amplified ssDNA after binding to streptavidin Sepharose beads (GE, UK) in an empty DNA synthesis column (Glen Research, USA). The eluted ssDNA was subsequently desalted (NAP-5 column, GE, UK), vacuum-dried, and redissolved in 50 µl of binding buffer to generate the input library for the next round of selection. After seven rounds of in vitro selection, the eluted DNA was PCR amplified, cloned into pCR®2.1-TOPO vector (Invitrogen), and sequenced.

A total of ninety-four different sequences were obtained and further assayed individually for its binding affinity and specificity to MAGE-A3$_{111-125}$. Plasmid DNA was first amplified by use of anchored PCR, as described above. The resulting ssDNA products were purified through 12% denaturing PAGE and incubated with the biotinylated peptide MAGE-A3$_{111-125}$, which was pre-incubated with the streptavidin-coupled magnetic beads and thus formed a peptide-magnetic bead complex through the streptavidin-biotin interaction. The sequences that bound specifically to the peptide MAGE-A3$_{111-125}$ were isolated by the magnet and subject to further purification, as the procedure described in library selection.

An oligonucleotide aptamer specifically bound to MAGE-A3$_{111-125}$ was chosen for the following analysis, which comprised in sequence: a 5'-end primer of ATCCAGAGT-GACGCAGCA (SEQ ID NO: 2), a central random region of AGCACTCAATATTCCC (SEQ ID NO: 1), and a 3'-end primer of TGGACACGGTGGCTTAGT (SEQ ID NO: 3). Such oligonucleotide aptamer was termed "Ap52," for it consisted of 52 nucleotides.

Example 2

Characterization of Ap52

Figure 2:
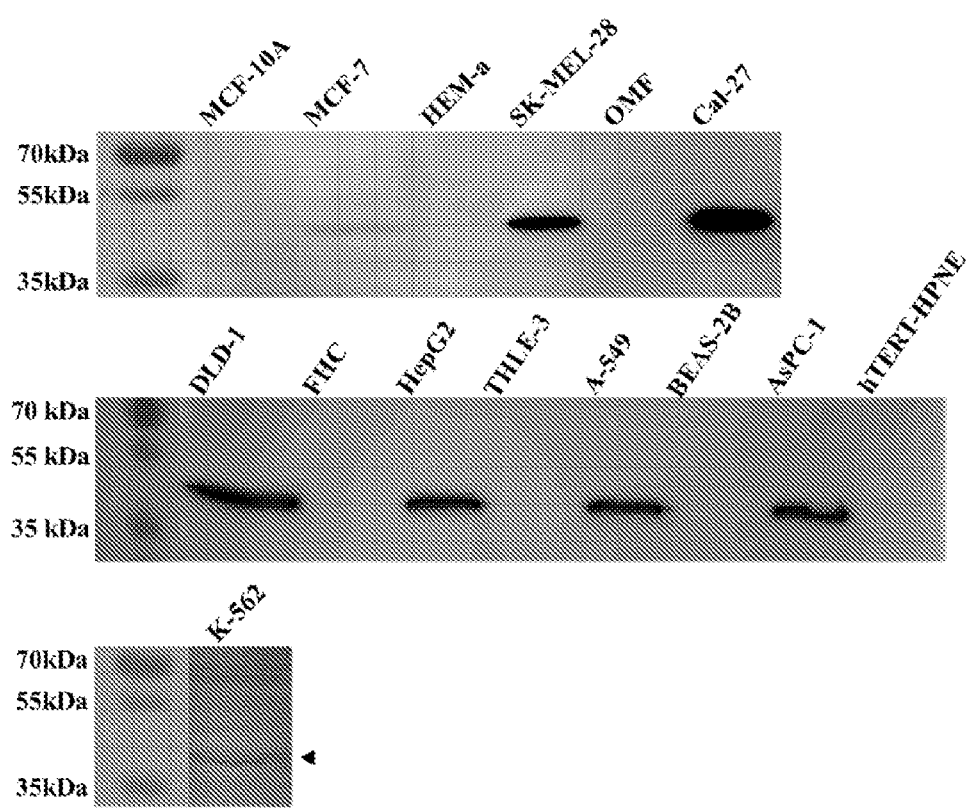
FIG. 2 is a photograph depicting the immuno-blot analysis of the expression of MAGE-A3 in the specified cancer cell lines according to Example 2 of the present disclosure.
Figure 3:
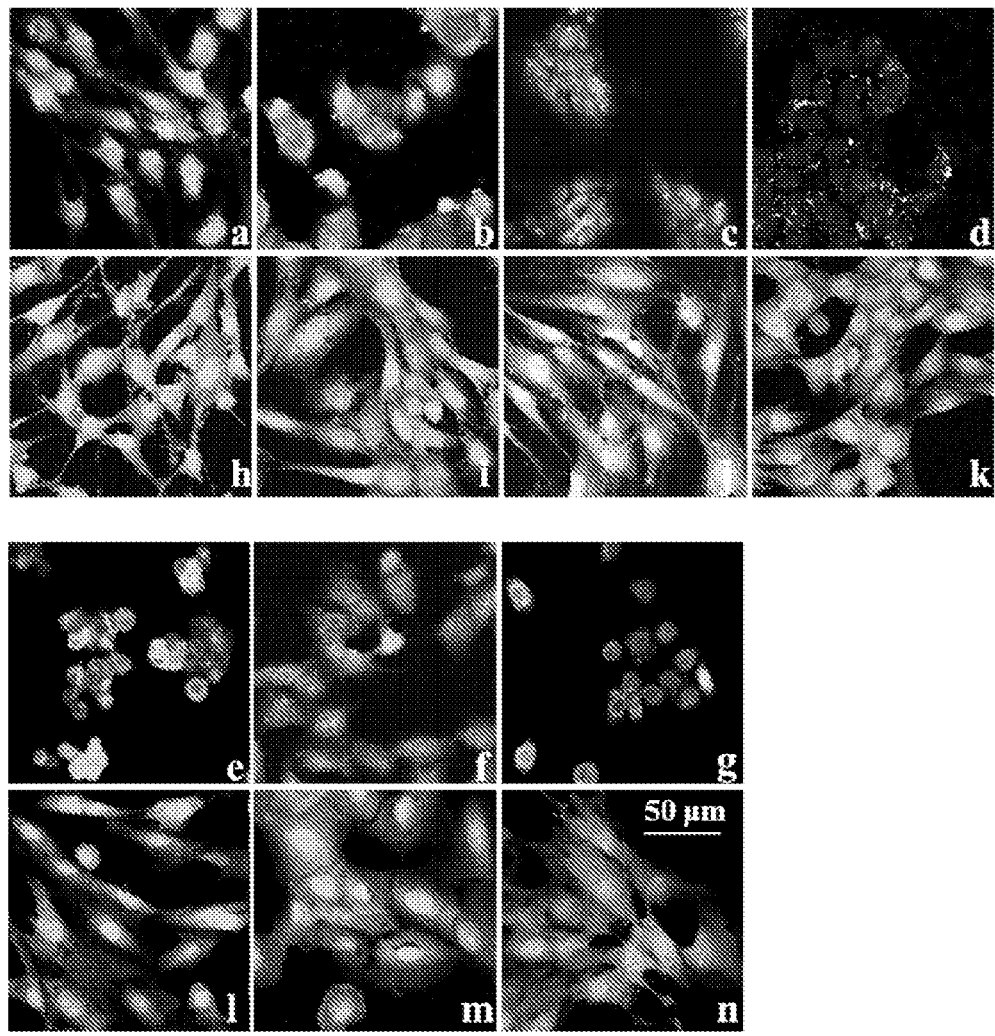
FIG. 3 are confocal laser scanning microscopy images illustrating the targeting of Cyanine 3 (Cy3)-conjugated Ap52 of Example 2 to various cell lines: (a) SK-MEL-28 cell, (b) MCF-7 cell, (c) Cal-27 cell, (d) DLD-1 cell, (e) HepG2 cell, (f) A549 cell, (g) AsPC-1 cell, (h) HEM-a cell, (i) MCF-10A cell, (j) OMF cell, (k) FHC cell, (l) THLE-3 cell, (m) BEAS-2B cell, or (n) hTERT-HPNE cell; all micrographs are merged images of Cy-3 (red, Ex. 561 nm), DAPI (blue, nuclear staining, Ex. 405 nm) and Calcein AM (green, cytoplasmic staining, Ex. 488 nm)
Figure 4:
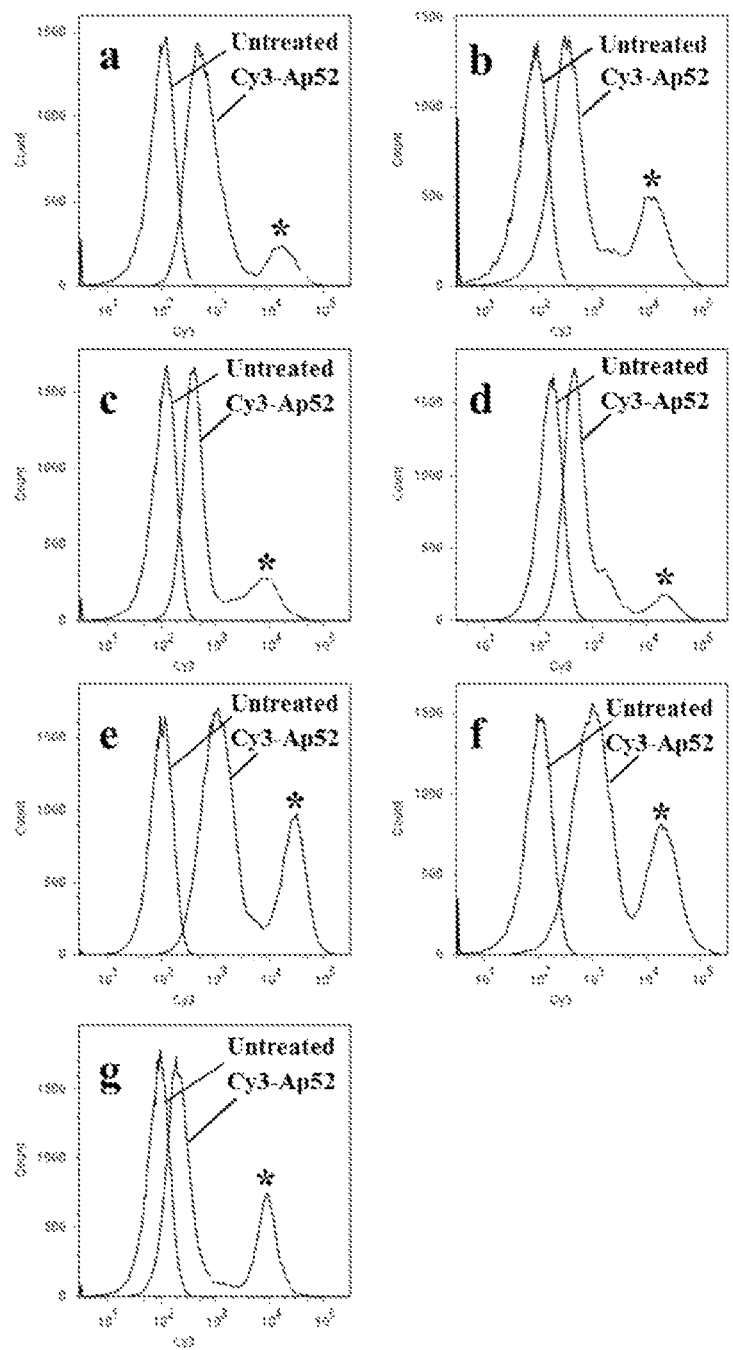
FIG. 4 are the data of flow cytometry assay that depicts the targeting of Cy3-conjugated Ap52 of Example 2 to various cancer cell lines: (a) MCF-7 cell, (b) DLD-1 cell, (c) HepG2 cell, (d) A549 cell, (e) SK-MEL-28 cell, (f) Cal-27 cell, and (g) AsPC-1 cell; right curve represents the binding of Cy3-conjugated Ap52 to the cells, binding fluorescence signals as asterisk indicated; untreated cells were used as a control (left curve as indicated line)
Figure 5:
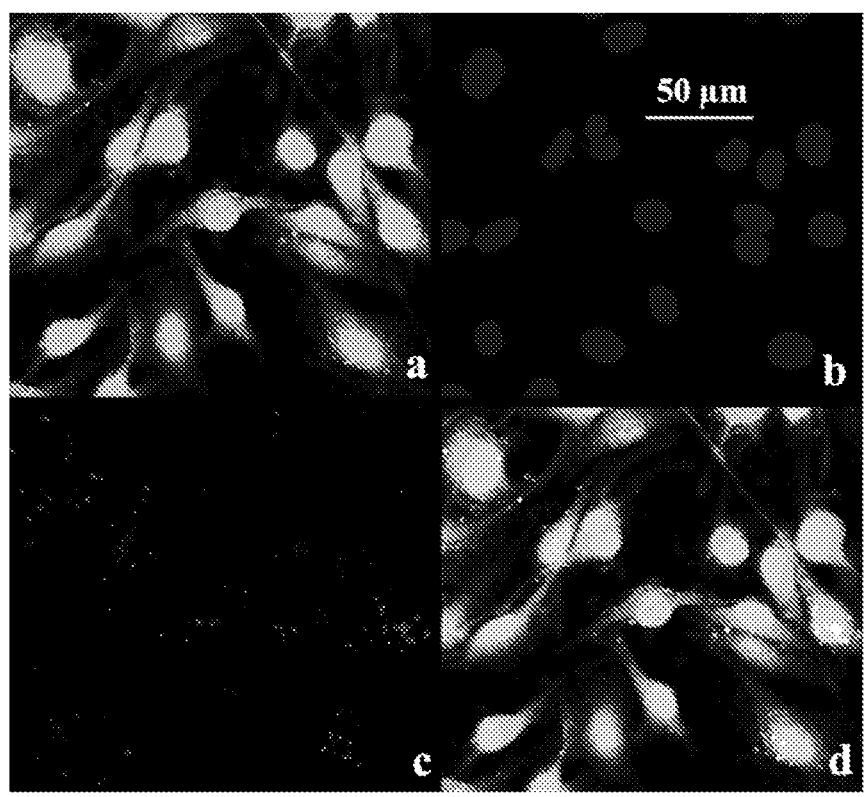
FIG. 5 are photographs of confocal laser scanning microscopy illustrating the targeting of Cy3-conjugated Ap52 of Example 2 to cancer cell line SK-MEL-28, in which the SK-MEL-28 cells were respectively treated with (a) Calcein AM (green, cytoplasmic staining, Ex. 488 nm), (b) DAPI (blue, nuclear staining, Ex. 405 nm), and (c) Cy3-conjugated Ap52 (red, Ex. 561 nm); (d) was the merged image of (a), (b), and (c)
Figure 6:
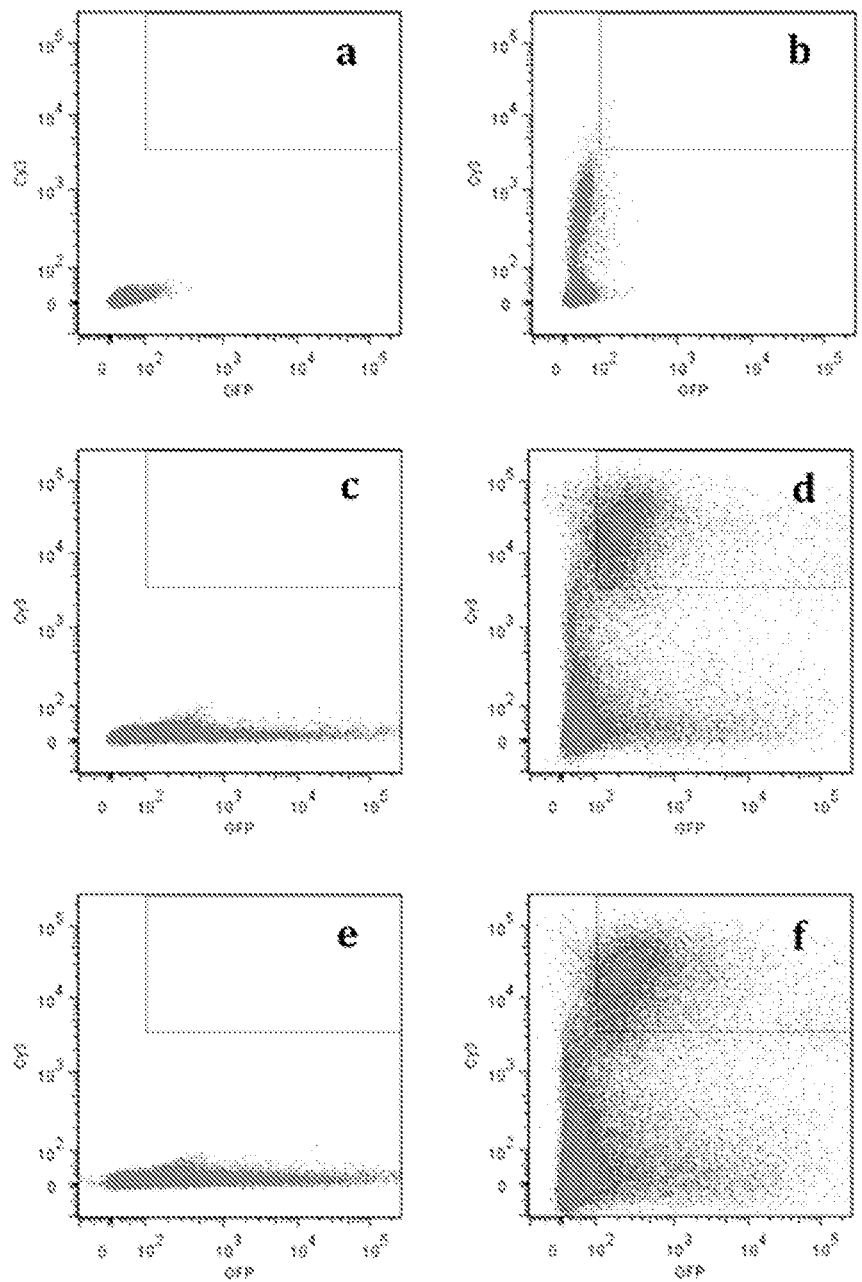
FIG. 6 are the data of flow cytometry assay that depicts the fluorescent level of (a) K-562 cell, (b) K-562 cell treated with Cy3-conjugated Ap52, (c) K-562 cell expressing GFP-tagged HLA-I, (d) K-562 cell expressing GFP-tagged HLA-I and treated with Cy3-Ap52, (e) K-562 cell expressing GFP-tagged HLA-II, or (f) K-562 cell expressing GFP-tagged HLA-II and treated with Cy3-Ap52, in which the double fluorescent population (upper right rectangle) in (d) and (f) represents the GFP-expressing cells bound to Cy3-conjugated Ap52.

The specificity of Ap52 of Example 1 to MAGE-A3 was further confirmed in this example, and results are presented in FIGS. 1 to 6, in which FIG. 1 illustrates the binding specificity of Ap52 to the MAGE-A3$_{111-125}$ peptide, while FIGS. 2 to 4 respectively illustrate the targeting selectivity of Ap52 to cancer cells having MAGE-A3 peptide expressed thereon, and FIGS. 5 and 6 characterize the expression site of MAGE-A3$_{111-125}$ in cancer cells recognized/targeted by the present Ap52 of Example 1.

2.1 the Specificity of Ap52 Toward MAGE-A3$_{111-125}$ Peptide

As evident from FIG. 1, Ap52 exhibited good affinity and specificity to MAGE-A3$_{111-125}$ (Lane labeled "+" under Panel labeled Ap52), but not to peptides from NY-ESO-1 (see FIG. 1, in which Lanes labeled N1, N2, and N3 respectively represent the epitopes 87-111, 119-143, and 157-170 of NY-ESO-1). This binding activity was also sequence-specific, for altering the flanking region with a 5'-end primer of ATAGGAGTCGACCGACAC (SEQ ID NO: 5) and a 3'-end primer of GTCTACATCTAAGCTCAT (SEQ ID NO: 6) resulted in nonspecific binding to streptavidin-coated magnetic beads, even in the absence of peptides (Lane labeled—under Panel PB). Thus, Ap52 is highly specific in terms of binding with MAGE-A3$_{111-125}$ peptide.

2.2 the Specificity of Ap52 Toward Cancer Cells Having MAGE-A3 Expressed Therein To investigate whether Ap52 targeted specifically toward cancer cells that express MAGE-A3, seven cancer cell lines and their corresponding normal cell lines were used in this example. They were MCF-7 (breast adenocarcinoma) and MCF-10A (fibrocystic disease); SK-MEL-28 (malignant melanoma) and HEM-a (human epidermal melanocyte primary cell); Cal-27 (tongue carcinoma) and OMF (oral mucosal fibroblasts); DLD-1 (colorectal adenocarcinoma) and FHC (colon epithelial cell); HepG2 (hepatocellular carcinoma) and THLE-3 (liver epithelial cell); A549 (lung carcinoma) and BEAS-2B (bronchial epithelial cell); and AsPC-1 (pancreas adenocarcinoma) and hTERT-HPNE (pancreas epithelial-like cell). Before the intended experiment started, the expression of MAGE-A3 in respective cancer cells was first confirmed by immunoblot analysis. As the data illustrated in FIG. 2, MAGE-A3 only expressed in the cancer cells, while no signal was detected in their corresponding normal cells.

To facilitate the observation of binding between Ap52 and MAGE-A3-expressing cells, Ap52 was conjugated with Cy3, and adherent cells were incubated with Ap52-Cy3 and continued cultured for 16, 24, and 48 hrs. The cells were pre-stained with Calcein AM to visualize the cytoplasm.

After aptamer binding and washing, the nuclei were subsequently counter-stained with DAPI. Laser scanning confocal microscopy revealed that the Cy3 signals were clearly visible in cells cultured for 48 hrs. As depicted in FIG. 3, Cy3 signals were observed in all seven types of cancer cells: SK-MEL-28 cell (FIG. 3a), MCF-7 cell (FIG. 3b), Cal-27 cell (FIG. 3c), DLD-1 cell (FIG. 3d), HepG2 cell (FIG. 3e), A549 cell (FIG. 3f), and AsPC-1 cell (FIG. 3g); whereas only background levels of signal were observed in their corresponding normal/noncancerous cells: HEM-a cell (FIG. 3h), MCF-10A cell (FIG. 3i), OMF cell (FIG. 3j), FHC cell (FIG. 3k), THLE-3 cell (FIG. 3l), BEAS-2B cell (FIG. 3m), and hTERT-HPNE cell (FIG. 3n). The abundance of the Ap52 signals more or less matched the MAGE-A3 protein levels detected by immunoblot analysis (comparing FIG. 2 with FIG. 3).

The binding specificity of Ap52 to cancer cell was further examined by flow cytometry assay. As the flow data illustrated in FIG. 4, compared with the untreated group, fluorescence signals (marked with asterisks) were observed in all the seven cancer cells, including MCF-7 cell (FIG. 4a), DLD-1 cell (FIG. 4b), HepG2 cell (FIG. 4c), A549 cell (FIG. 4d), SK-MEL-28 cell (FIG. 4e), Cal-27 cell (FIG. 4f), and AsPC-1 (FIG. 4g), treated with Cy3-conjugated Ap52. Particularly, higher level of fluorescence signals reflecting the MAGE-A3 protein levels detected by immunoblot analysis were observed in the DLD-1 cell (FIG. 4b), SK-MEL-28 cell (FIG. 4e), and Cal-27 cell (FIG. 4f), as compared with those in other cancer cells (comparing FIG. 2 with FIG. 4).

All the data indicated that Ap52 possessed targeting specificity to various MAGE-A3-expressing cancer cells, but not to MAGE-A3-nonexpressing normal/noncancerous cells.

2.3 the Subcellular Localization of MAGE-A3$_{111-125}$ Recognized by Ap52

Figure 10:
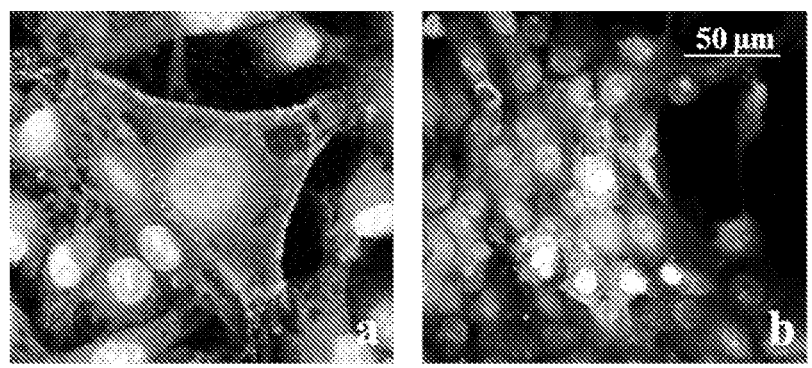
FIG. 10 are confocal laser scanning microscopy images illustrating the targeting of Cy3-conjugated Ap16 of Example 3 to melanoma cell line SK-MEL-28 (a) and oral cancer cell line Cal-27 (b); all micrographs are merged images of Cy-3 (red, Ex. 561 nm), DAPI (blue, nuclear staining, Ex. 405 nm) and Calcein AM (green, cytoplasmic staining, Ex. 488 nm)

Referring to FIG. 3, the Cy3-conjugated aptamer signals in the cancer cells are apparently located either on the cell surface or along the periphery of the cell. To confirm whether the MAGE-A3$_{111-125}$ recognized by the present Ap52 was mainly localized to the cell surface, the SK-MEL-28 cells were respectively treated with Calcein AM (cytoplasmic staining, FIG. 5a), DAPI (nuclear staining, FIG. 5b), and Cy3-conjugated aptamer (FIG. 5c). The merged image (FIG. 5d) revealed that Cy3-conjugated Ap52 specifically targeted to the surface of SK-MEL-28 cells, but not the cytoplasm or nucleus. Such finding was subsequently confirmed by serial images taken along Z-axis of cancer cell line SK-MEL-28 in FIG. 10, which indicated that the signal emitted by Cy3-conjuated Ap52 was mainly expressed on the periphery or covering the entire cell surface.

Accordingly, the MAGE-A3$_{111-125}$ recognized by Ap52 was mainly presented on the cell membranes of cancer cells.

2.4 Presentation of MAGE-A3 Peptide by MHC Molecule

In this example, cells devoid of MHC but positively express full length MAGE-A3 protein (i.e., K-562 cells) were used to confirm the targeting specificity of Ap52, which specifically recognized the MAGE-A3$_{111-125}$ peptide, but not the full length protein. Results are depicted in FIG. 6.

According to the flow cytometric analysis, K-562 cells were unable to bind to Cy3-conjugated Ap52 (FIG. 6). However, when the cells were transfected with a GFP-tagged cDNA clone so as to transiently express MHC protein, the binding of Ap52 toward the cells became evident (FIGS. 6c-f), and either MHC class I (i.e., HLA I or HLA-A) or MHC class II (i.e., HLA II or HLA-DRB4) protein was effective (see FIGS. 6d and 6f) in inducing the binding of Cy3-Ap52 toward the cells, presumably having peptides within MAGE-A3$_{111-125}$ region presented thereon. The quantified result of the flow cytometric analysis is summarized in Table 1.

TABLE 1

Ap52 bound to cells having MHC-presented MAGE-A3 peptides thereon

|  | GFP positive (%) | GFP and Cy3 double positive (%) |
|---|---|---|
| K-562 | 1.21 | 0.8 |
| HLA-I | 38.2 | 23.8 |
| HLA-II | 46.8 | 22.3 |

The number is the percentage of GFP positive counts or GFP and Cy3 double positive counts in 50,000 counting events, and is the average of two independent experiments.

The data of this example indicated that Ap52 specifically recognizes and targets MAGE-A3$_{111-125}$, which was presented onto the cell surface by a variety of HLA alleles.

2.5 Modification of Ap52

In order to increase DNA stability in a physiological fluid, a modified Ap52 (designated ThioAp52), with phosphorothioate substitutes at seven sites, was generated. Nuclease resistance of aptamers was tested in serum containing medium. As illustrated in Table 2, the amount of unmodified Ap52 reduced to approximately 20% after 6 hr, and to 10% after 24 hr, whereas about 50% and 30% of ThioAp52 still remained after 6 hr and 24 hr, respectively. Conjugating the Ap52 with Cy3 (Cy3-conjugated Ap52) also substantially improved the stability of the aptamer during the course of the 24-hr assay, and the two types of modifications appeared to have synergistic effect (Table 2). Thus, future diagnostic and therapeutic applications can be achieved through the use of various chemically modified aptamers.

TABLE 2

Aptamer stability assay

| Name | Time | | | | | |
|---|---|---|---|---|---|---|
|  | 0 h | 1 h | 2 h | 6 h | 12 h | 24 h |
| Ap52[1] | 100 | 64 | 47 | 22 | 19 | 13 |
| ThioAp52[2] | 100 | 91 | 73 | 48 | 35 | 30 |
| Cy3-Ap52[2] | 100 | 75 | 50 | 45 | 38 | 29 |
| Cy3-ThioAp52[2] | 100 | 92 | 82 | 58 | 46 | 40 |

[1]The number is the percentage of aptamers remained in the test medium during the time course, and is the average of two independent experiments.
[2]ThioAp52 = phosphorothioate modification of Ap52. Cy3-Ap52 and Cy3-ThioAp52 are Cy3-conjugates of Ap52 and ThioAp52, respectively.

The data of examples 2.1 to 2.5 demonstrated that Ap52, not only exhibited binding specificity to MAGE-A3$_{111-125}$ peptide in vitro, but also possessed excellent targeting selectivity to MAGE-A3$_{111-125}$ peptide presented by a MHC molecule to the surface of the cancer cell. Further, data from this example also confirmed that suitable modification of Ap52 (i.e., adding phosphorothioate substitutes thereto, or fluorescent dye conjugation) can enhance the aptamer stability.

Example 3

Characterization of Ap16

As evidenced in SELEX procedures, the affinity and specificity of the aptamer were primarily influenced by the central randomized region, and the sequences upstream and downstream to the central randomized region might provide additional recognition of the aptamer to the target. Thus, to evaluate whether the central randomized region exhibits similar targeting ability to MAGE-A3$_{111\text{-}125}$ as that of Ap52, the central randomized region of Ap52 having 16 nucleotides, i.e., AGCACTCAATATTCCC (SEQ ID NO: 1, hereinafter "Ap16") was examined by the analysis of binding affinity.

3.1 Binding Affinity of Ap16 or Ap52 to MAGE-A3$_{111\text{-}125}$

Figure 7A:
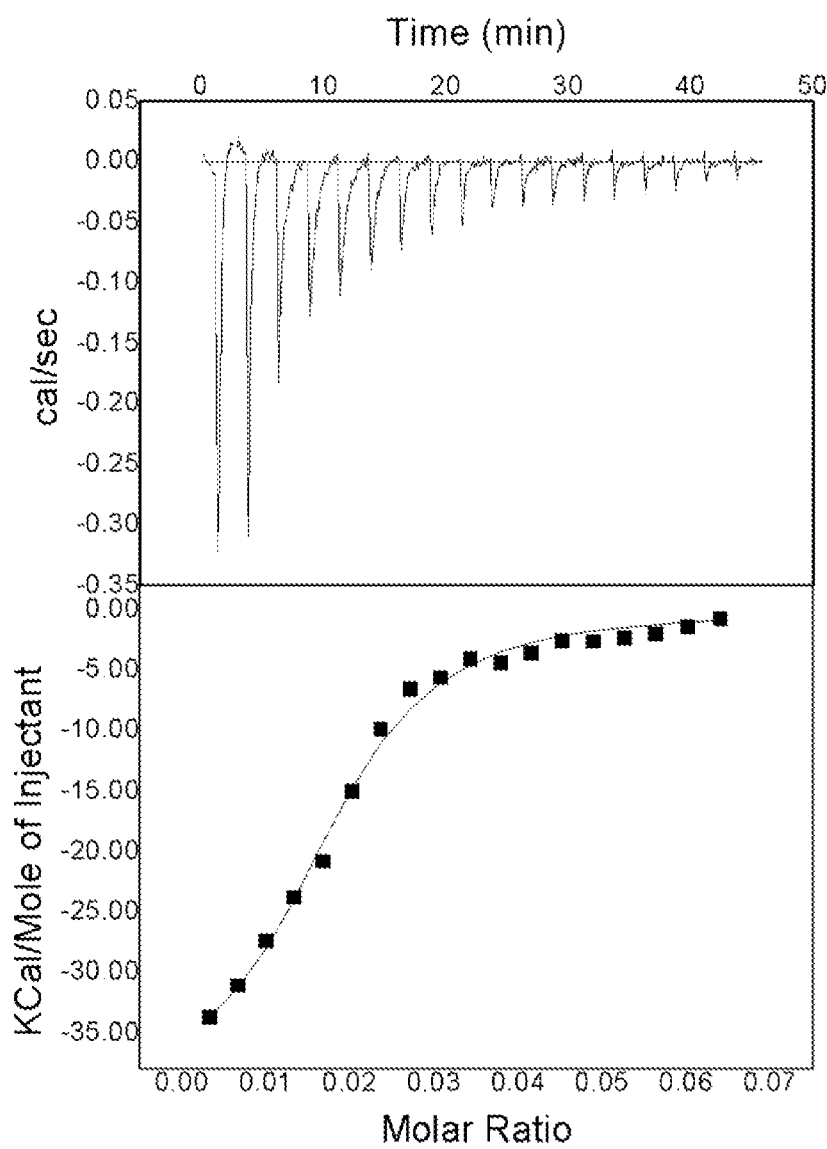
FIGS. 7A and 7B illustrate the respective interactions between oligonucleotide aptamers Ap52 of Example 2 (FIG. 7A) or Ap16 of Example 3 (FIG. 7B) and the MAGE-A3$_{111-125}$ peptide; in which the interaction is determined by isothermal titration calorimetry; the top panels are raw titration data, which show the heat resulting from the injection of aptamer into the peptide, and each peak represents an injection; the bottom panels are the titration curve, which show the integrated heat of each titration; thermodynamic parameters obtained from fitting the titration data with one-set-of sites binding model (MicroCal Origin 7): Ap16, $K_d$=95 nM, $\Delta H$ =−41 kcal/mol; Ap52, $K_d$=57 nM, $\Delta H$=−24 kcal/mol.
Figure 7B:
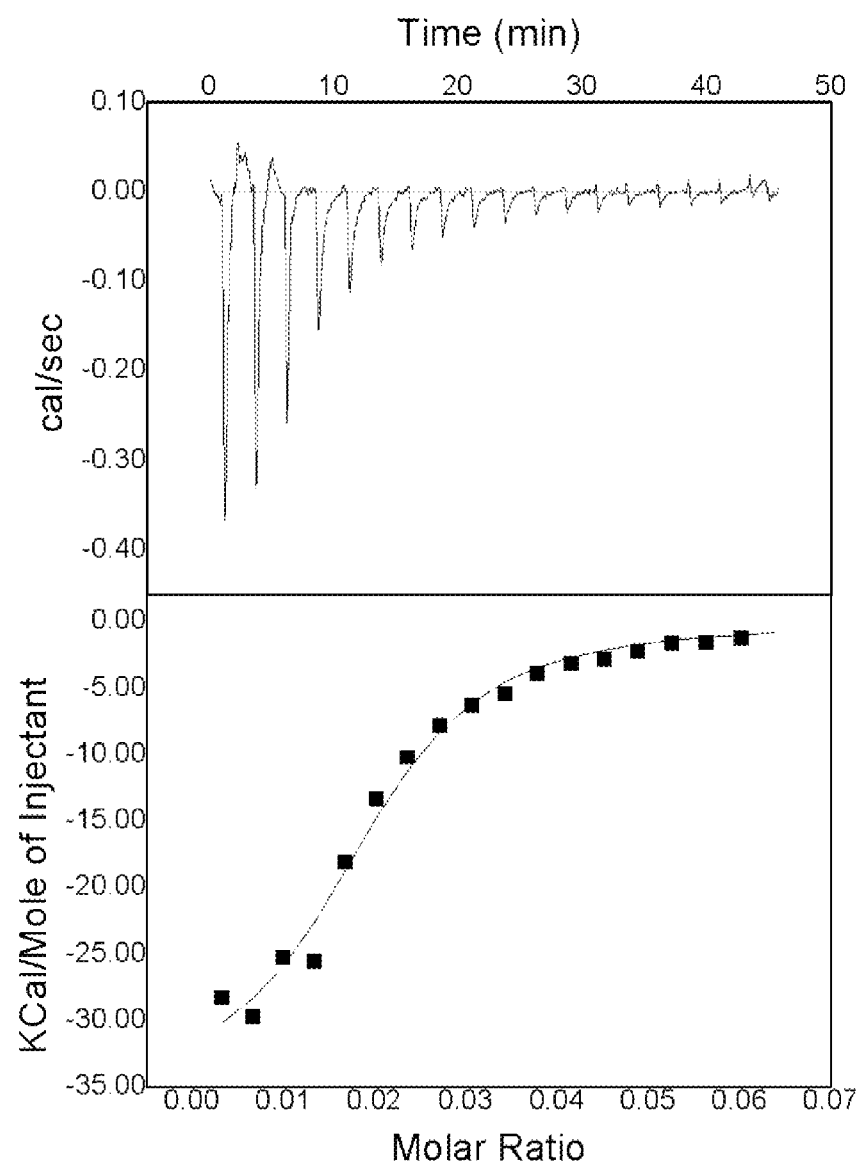

Isothermal titration calorimetry (ITC) is a technique used to measure the thermodynamic profile of the interactions between two molecules, and thus can be used to determine the respective binding affinities of Ap16 and Ap52 to MAGE-A3$_{111\text{-}125}$ peptide. Results are provided in FIGS. 7A and 7B. The binding affinities of peptide MAGE-A3$_{111\text{-}125}$ to Ap16 (FIG. 7A) and Ap52 (FIG. 7B) differed by less than 2-folds, and the dissociation constants were 95 and 57 nM, respectively. Therefore, both Ap52 and Ap16 are effective in targeting MAGE-A3$_{111\text{-}125}$-peptide.

3.2 the Specificity of Ap16 to Cancer Cells

Figure 8:
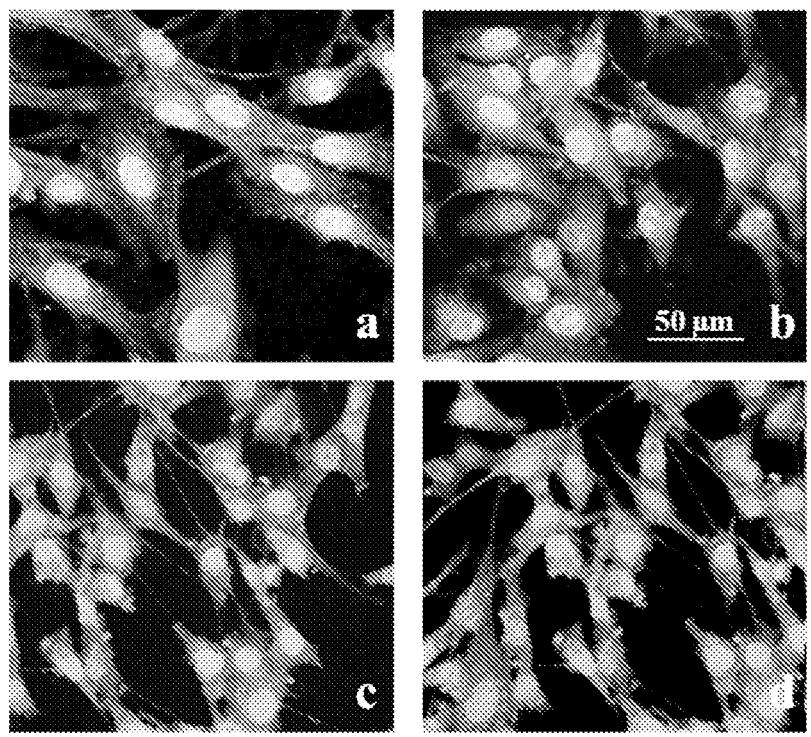
FIG. 8 are confocal laser scanning microscopy images illustrating the targeting of Cy3-conjugated Ap16 of Example 3 to skin cancer cell line SK-MEL-28 (a) or the corresponding normal cell line HEM-a (c); as a targeting control, Cy3-conjugated Ap16-control of Example 3 were also incubated with SK-MEL-28 (b) or HEM-a (d); all micrographs are merged images of Cy-3 (red, Ex. 561 nm), DAPI (blue, nuclear staining, Ex. 405 nm) and Calcein AM (green, cytoplasmic staining, Ex. 488 nm)

In view of the results of Example 3.1, the cell targeting capability of Ap16 was further examined in a malignant melanoma cell line SK-MEL-28. Ap16 was first conjugated with Cy3 and the Cy3-conjugated Ap16 was then incubated with SK-MEL-28 cell in accordance with the procedures described above. The interaction between Ap16 and SK-MEL-28 cells was monitored by following the fluorescence signal given off by Cy3 using confocal laser scanning microscopy. As depicted in FIG. 8a, Cy3-conjugated Ap16 effectively bound to each SK-MEL-28 cells on the cell surface and along the cell periphery. The Ap16-Cy3 signal levels were similar to or higher than those resulting from the binding of Cy3-conjugated Ap52 (data not shown). A 16-nucleotide region (SEQ ID NO: 7, herein after "Ap16-control") from another oligonucleotide was selected from SELEX, failed to bind to MAGE-A3$_{111\text{-}125}$ in the validating binding assay, and was used as a negative control. Cy3 conjugated Ap16-control did not produce any signals above background level in SK-MEL-28 cells (FIG. 8b). In contrast, normal HEM-a cells incubated with Cy3 conjugates of either Ap16 (FIG. 8c) or Ap16-control (FIG. 8d) failed to produce any fluorescent signals, which indicates that no interactions between Ap16 and the normal HEM-a cells. These results indicated that Ap16 sequence is sufficient and critical for specifically targeting the MAGE-A3$_{111\text{-}125}$ peptide antigen on the cell surface.

Figure 9:
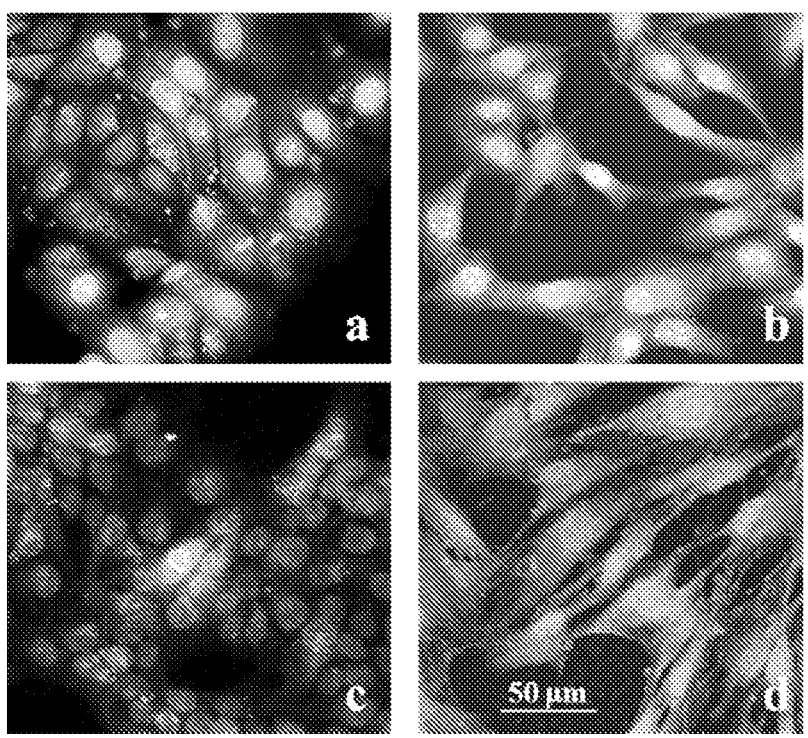
FIG. 9 are confocal laser scanning microscopy images illustrating the targeting of Cy3-conjugated Ap16 of Example 3 to breast cancer cell line MCF-7 (a), breast normal cell line MCF-10A (b), oral cancer cell line Cal-27 (c), and oral normal cell line OMF (d); all micrographs are merged images of Cy-3 (red, Ex. 561 nm), DAPI (blue, nuclear staining, Ex. 405 nm) and Calcein AM (green, cytoplasmic staining, Ex. 488 nm)
Figure 11:
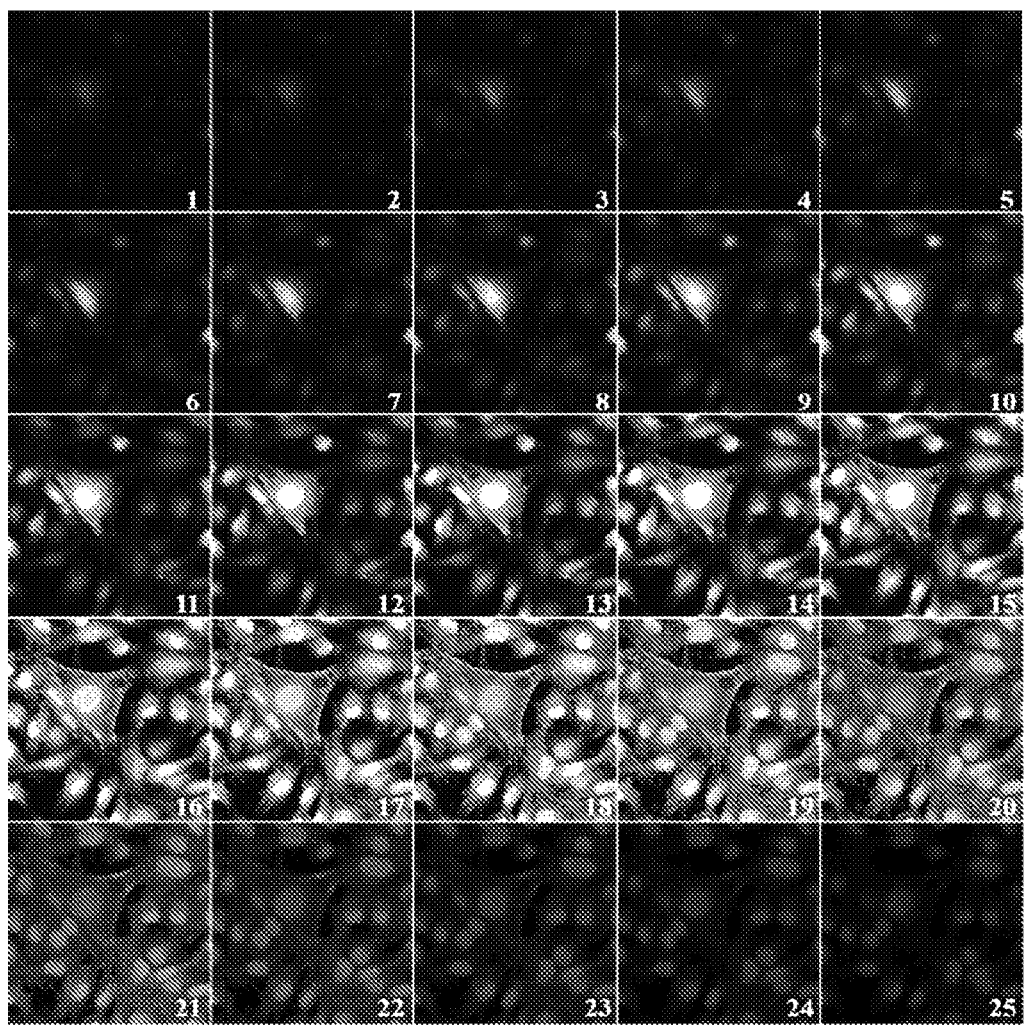
FIG. 11 are confocal laser scanning microscopy images of Z-axis serial images of SK-MEL-28 cell line treated with Cy3-conjugated Ap16 of Example 3; all micrographs are merged images of Cy-3 (red, Ex. 561 nm), DAPI (blue, nuclear staining, Ex. 405 nm) and Calcein AM (green, cytoplasmic staining, Ex. 488 nm).

In addition to melanoma cells, Ap16 was also examined for its binding affinity towards other types of cancer cells. Results in FIG. 9 confirmed that, indeed, Cy3-conjugated Ap16 may successfully target the surface of breast cancer cell line MCF-7 (FIG. 9a) and oral cancer cell line Cal-27 (FIG. 9c), but not breast normal cell line MCF-10A (FIG. 9b) and oral normal cell line OMF (FIG. 9d). The confocal microscopy images of SK-MEL-28 melanoma cell cells (FIG. 10a) and Cal-27 oral cancer cells (FIG. 10b) also confirmed that some cells exhibited fluorescent signals along the periphery or covering the entire cell surface. FIG. 11 provides photographs of serial images of the cells in FIG. 10a taken along the z-axis, in which the number represented the serial dissection of SK-MEL-28 melanoma cells in sequence. In sum, Ap16 also exhibited targeting specificity to cancer cells with MAGE-A3 expression, as Ap52 did.

As afore-mentioned, the upstream and downstream sequences of the aptamer might be involved in the full structure and function of the aptamer, and thus in some situations, the sequences might be indispensable. However, in the present invention, the data above indicated that Ap16 or the central randomized region of Ap52 alone, is sufficient enough for effectively and specifically targeting MAGE-A3$_{111\text{-}125}$. For certain applications requiring shorter oligonucleotides, Ap16 might meet the requirement and thus substitute for Ap52.

In conclusion, the characterization of Ap52 and Ap16 with the binding affinity and specificity to tumor-specific MAGE-A3 antigen confirms the potential use of these molecules for targeting multiple types of cancer cells. Compared with other reagents, the advantages of aptamers and the ease of synthesizing peptides for use in SELEX screening indicate the potential for generating a great variety of aptamers against a considerable number of tumor-specific antigens. Consequently, the oligonucleotide aptamer of the present invention might be used to effectively target cancer cells for diagnostic and/or therapeutic purposes.

It will be understood that the above description of embodiments is given by way of example only and that various modifications may be made by those with ordinary skill in the art. The above specification, examples and data provide a complete description of the structure and use of exemplary embodiments of the invention. Although various embodiments of the invention have been described above with a certain degree of particularity, or with reference to one or more individual embodiments, those with ordinary skill in the art could make numerous alterations to the disclosed embodiments without departing from the spirit or scope of this invention.

What is claimed is:

1. An oligonucleotide aptamer for targeting a peptide presented by a major histocompatibility complex (MHC) on the surface of a cell comprising the sequence of SEQ ID NO: 1.

2. The oligonucleotide aptamer of claim 1, wherein the peptide is derived from melanoma-associated antigen A3 (MAGE-A3).

3. The oligonucleotide aptamer of claim 2, wherein the peptide has the amino acid sequence of SEQ ID NO: 4.

4. The oligonucleotide aptamer of claim 1, further comprising the sequences of SEQ ID NO: 2 and SEQ ID NO: 3, respectively disposed at and connected thereto, the upstream and downstream of SEQ ID NO: 1.

5. The oligonucleotide aptamer of claim 1, wherein the cell is derived from a tumor selected from the group consisting of melanomas, leukemia, tongue carcinoma, colorectal carcinoma, esophageal carcinoma, gastric carcinoma, lung cancer, multiple myeloma, bladder cancer, breast cancer, pancreatic cancer, renal cancer, hepatocellular carcinoma, ovarian cancer, prostate cancer, and head and neck squamous cell carcinoma.

6. The oligonucleotide aptamer of claim 1, wherein the oligonucleotide aptamer is modified with one or more chemical groups that is 2'-aminopyrimidinyl group, 2'-O-methylpurinyl group, 5'-dialkyl group, phosphorothioate cap, 2'-OH nucleotides, 2'-fluoropyrimidine or 5-(1-pentynyl)-2'-deoxyuridine.

7. The oligonucleotide aptamer of claim 1, wherein the oligonucleotide aptamer is conjugated with a fluorescent dye, a reporter molecule, a contrast agent, an anti-cancer drug, a peptide or a magnetic particle.

8. A composition for targeting a cell having a peptide presented by MHC on its surface comprising the oligonucleotide aptamer of claim 1, and a pharmaceutically acceptable excipient.

9. The composition of claim 8, wherein the peptide is derived from MAGE-A3.

10. The composition of claim 9, wherein the peptide has the amino acid sequence of SEQ ID NO: 4.

11. The composition of claim 8, wherein the oligonucleotide aptamer further comprises the sequences of SEQ ID NO: 2 and SEQ ID NO: 3 respectively disposed at and connected thereto, the upstream and downstream of SEQ ID NO: 1.

12. The composition of claim 8, wherein the cell is derived form a tumor selected from the group consisting of melanomas, leukemia, tongue carcinoma, colorectal carcinoma, esophageal carcinoma, gastric carcinoma, lung cancer, multiple myeloma, bladder cancer, breast cancer, pancreatic cancer, renal cancer, hepatocellular carcinoma, ovarian cancer, prostate cancer, and head and neck squamous cell carcinoma.

13. The composition of claim 8, wherein the oligonucleotide aptamer is modified with one or more chemical groups that is 2'-aminopyrimidinyl group, 2'-O-methylpurinyl group, 5'-dialkyl group, phosphorothioate cap, 2'-OH nucleotides, 2'-fluoropyrimidine or 5-(1-pentynyl)-2'-deoxyuridine.

14. The composition of claim 8, wherein the oligonucleotide aptamer is conjugated with a fluorescent dye, a reporter molecule, a contrast agent, an anti-cancer drug, a peptide or a magnetic particle.

15. A method of treating a subject suspected of having or suffering from a tumor comprising administering to the subject a therapeutically effective amount of the oligonucleotide aptamer of claim 1 to alleviate or ameliorate the progression of the tumor.

16. The method of claim 15, wherein the oligonucleotide aptamer further comprises the sequences of SEQ ID NO: 2 and SEQ ID NO: 3 respectively disposed at and connected thereto, the upstream and downstream of SEQ ID NO: 1.

17. The method of claim 15, wherein the tumor is characterized in having a peptide of SEQ ID NO:4 expressed thereon.

18. The method of claim 17, wherein the tumor is selected from the group consisting of melanomas, leukemia, tongue carcinoma, colorectal carcinoma, esophageal carcinoma, gastric carcinoma, lung cancer, multiple myeloma, bladder cancer, breast cancer, pancreatic cancer, renal cancer, hepatocellular carcinoma, ovarian cancer, prostate cancer, and head and neck squamous cell carcinoma.

19. The method of claim 15, wherein the oligonucleotide aptamer is conjugated with an anti-cancer drug.

20. The method of claim 15, wherein the oligonucleotide aptamer is modified with one or more chemical groups that is 2' aminopyrimidinyl group, 2'-O-methylpurinyl group, 5'-dialkyl group, phosphorothioate cap, 2'-OH nucleotides, 2'-fluoropyrimidine or 5-(1-pentynyl)-2'-deoxyuridine, to enhance the stability of the oligonucleotide aptamer.

\* \* \* \* \*

SEQUENCE LISTING

```
<160> NUMBER OF SEQ ID NOS: 7

<210> SEQ ID NO 1
<211> LENGTH: 16
<212> TYPE: DNA
<213> ORGANISM: Artificial Sequence
<220> FEATURE:
<223> OTHER INFORMATION: Ap16

<400> SEQUENCE: 1
agcactcaat attccc                                                     16

<210> SEQ ID NO 2
<211> LENGTH: 18
<212> TYPE: DNA
```

```
<213> ORGANISM: Artificial Sequence
<220> FEATURE:
<223> OTHER INFORMATION: upstreamed sequence of Ap16

<400> SEQUENCE: 2
atccagagtg acgcagca                                                 18

<210> SEQ ID NO 3
<211> LENGTH: 18
<212> TYPE: DNA
<213> ORGANISM: Artificial Sequence
<220> FEATURE:
<223> OTHER INFORMATION: downstreamed sequence of Ap16

<400> SEQUENCE: 3
tggacacggt ggcttagt                                                 18

<210> SEQ ID NO 4
<211> LENGTH: 15
<212> TYPE: PRT
<213> ORGANISM: Artificial Sequence
<220> FEATURE:
<223> OTHER INFORMATION: MAGE-A3 peptide

<400> SEQUENCE: 4

Arg Lys Val Ala Glu Leu Val His Phe Leu Leu Leu Lys Tyr Arg
1               5                   10                  15

<210> SEQ ID NO 5
<211> LENGTH: 18
<212> TYPE: DNA
<213> ORGANISM: Artificial Sequence
<220> FEATURE:
<223> OTHER INFORMATION: upstreamed sequence of PB

<400> SEQUENCE: 5
ataggagtcg accgacac                                                 18

<210> SEQ ID NO 6
<211> LENGTH: 18
<212> TYPE: DNA
<213> ORGANISM: Artificial Sequence
<220> FEATURE:
<223> OTHER INFORMATION: downstreamed sequence of PB

<400> SEQUENCE: 6
gtctacatct aagctcat                                                 18

<210> SEQ ID NO 7
<211> LENGTH: 16
<212> TYPE: DNA
<213> ORGANISM: Artificial Sequence
<220> FEATURE:
<223> OTHER INFORMATION: Ap16-negative control

<400> SEQUENCE: 7
atcattcgga tgtgtg                                                   16
```